United States Patent
Krull et al.

(10) Patent No.: US 8,974,743 B2
(45) Date of Patent: *Mar. 10, 2015

(54) DEVICE FOR CONTINUOUSLY CARRYING OUT CHEMICAL REACTIONS AT HIGH TEMPERATURES

(75) Inventors: Matthias Krull, Harxheim (DE); Roman Morschhaeuser, Mainz (DE)

(73) Assignee: Clariant Finance (BVI) Limited, Tortola (VG)

( * ) Notice: Subject to any disclaimer, the term of this patent is extended or adjusted under 35 U.S.C. 154(b) by 112 days.

This patent is subject to a terminal disclaimer.

(21) Appl. No.: 13/378,258

(22) PCT Filed: Jun. 9, 2010

(86) PCT No.: PCT/EP2010/003443
§ 371 (c)(1),
(2), (4) Date: Dec. 14, 2011

(87) PCT Pub. No.: WO2011/000460
PCT Pub. Date: Jan. 6, 2011

(65) Prior Publication Data
US 2012/0088885 A1    Apr. 12, 2012

(30) Foreign Application Priority Data
Jun. 30, 2009    (DE) .......................... 10 2009 031 059

(51) Int. Cl.
*A62D 3/00* (2006.01)
*C07C 1/32* (2006.01)
(Continued)

(52) U.S. Cl.
CPC ............... *C07C 1/321* (2013.01); *B01J 19/126* (2013.01); *C07C 67/08* (2013.01); *C07C 231/02* (2013.01);
(Continued)

(58) Field of Classification Search
CPC .... B01J 19/00; B01J 19/0013; B01J 19/0053; B01J 19/0093; B01J 19/20; B01J 19/24; B01J 7/00; B01J 10/00; B01J 8/00; B01J 8/001; B01J 8/008; B01J 8/02; B01J 8/025; B01J 8/0285; B01J 8/0486; B01J 8/067; B01J 12/00; B01J 2219/00094; H05B 6/64; H05B 6/6402; H05B 6/6408; H05B 6/6447; H05B 6/647; H05B 6/68; H05B 6/70; H05B 6/701; H05B 6/705; H05B 6/80; H05B 6/802; H05B 1/0244; H05B 6/00; H05B 6/60; H05B 1/00; H05B 1/02; A62D 3/00; A62D 3/10; A62D 3/17; A62D 3/178

USPC .......... 422/129, 187, 198, 199; 219/678, 686, 219/702, 704, 710, 745, 746, 750, 756, 757

See application file for complete search history.

(56) References Cited

U.S. PATENT DOCUMENTS 1,972,142 A    9/1934    Goldstein
2,601,561 A    6/1952    Schertz
(Continued)

FOREIGN PATENT DOCUMENTS

CH    681586    4/1993
CN    1228910    9/1999
(Continued)

OTHER PUBLICATIONS

Machine translation of EP 1291077 A2, which was published Mar. 12, 2003.*
(Continued)

*Primary Examiner* — Natasha Young
(74) *Attorney, Agent, or Firm* — Tod A. Waldrop (57) ABSTRACT

The invention relates to a device for continuously carrying out chemical reactions. The device comprises a microwave generator, a microwave applicator accommodating a microwave-transparent tube, and an isothermal reaction section which is arranged such that the material to be reacted is guided inside the microwave-transparent tube through a microwave applicator which is used as the heating zone and in which it is heated to reaction temperature by means of microwaves that are emitted from the microwave generator into the microwave applicator. The material to be reacted, which is heated and optionally under pressure, is transferred from the microwave applicator to an isothermal reaction zone once it has left the heating zone, said reaction zone being arranged downstream of the heating zone, and is cooled once it has left the isothermal reaction zone.

14 Claims, 2 Drawing Sheets

(51) Int. Cl.
  *B01J 19/12* (2006.01)
  *C07C 67/08* (2006.01)
  *C07C 231/02* (2006.01)
  *C07D 307/60* (2006.01)
  *H05B 6/80* (2006.01)
  *B01J 19/00* (2006.01)
  *B01J 19/24* (2006.01)
  *B01J 7/00* (2006.01)
  *B01J 8/00* (2006.01)
  *B01J 10/00* (2006.01)
  *B01J 12/00* (2006.01)
  *H05B 6/64* (2006.01)
  *H05B 6/68* (2006.01)
  *H05B 6/70* (2006.01)
  *A62D 3/10* (2007.01)
  *A62D 3/17* (2007.01)

(52) U.S. Cl.
  CPC ............... C07D 307/60 (2013.01); H05B 6/80 (2013.01); H05B 6/806 (2013.01); *B01J 2219/0871* (2013.01); *B01J 2219/1227* (2013.01); *C07C 2531/24* (2013.01)
  USPC ........... 422/199; 422/129; 422/187; 422/198; 219/678; 219/686; 219/702; 219/704; 219/710; 219/745; 219/746; 219/750; 219/756; 219/757

(56) References Cited

U.S. PATENT DOCUMENTS

| | | |
|---|---|---|
| 3,024,260 A | 3/1962 | Ernst |
| 3,050,418 A | 8/1962 | Mendelsohn et al. |
| 3,113,026 A | 12/1963 | Sprung |
| 3,197,473 A | 7/1965 | Klosa |
| 3,395,162 A | 7/1968 | Lamberti |
| 3,585,224 A | 6/1971 | Friedrich et al. |
| 3,652,434 A | 3/1972 | Bar-Nun et al. |
| 3,652,671 A | 3/1972 | Barron |
| 3,682,946 A | 8/1972 | Liechti |
| 3,836,551 A | 9/1974 | Schroeder et al. |
| 4,133,833 A | 1/1979 | Hull |
| 4,165,311 A | 8/1979 | Isowa et al. |
| 4,221,948 A | 9/1980 | Jean |
| 4,339,648 A | 7/1982 | Jean |
| 4,582,933 A | 4/1986 | Mertens et al. |
| 4,675,319 A | 6/1987 | Nardi et al. |
| 4,859,796 A | 8/1989 | Hurtel et al. |
| 4,994,541 A | 2/1991 | Dell et al. |
| 5,114,684 A | 5/1992 | Walker |
| 5,185,466 A | 2/1993 | Kozulic et al. |
| 5,304,766 A | 4/1994 | Baudet et al. |
| 5,326,538 A | 7/1994 | Walker |
| 5,387,397 A | 2/1995 | Strauss et al. |
| 5,419,815 A | 5/1995 | Doerpinghaus et al. |
| 5,646,318 A | 7/1997 | Dery et al. |
| 5,646,319 A | 7/1997 | Letton et al. |
| 5,710,295 A | 1/1998 | Woodbury et al. |
| 5,830,953 A | 11/1998 | Nishikawa et al. |
| 5,856,538 A | 1/1999 | Strecker et al. |
| 5,866,531 A | 2/1999 | Assmann et al. |
| 5,892,115 A | 4/1999 | Aizawa et al. |
| 5,988,877 A | 11/1999 | Hochrad et al. |
| 6,017,426 A | 1/2000 | Semeria et al. |
| 6,107,498 A | 8/2000 | Maisonneuve et al. |
| 6,120,741 A * | 9/2000 | Jacquault et al. ............. 422/199 |
| 6,121,471 A | 9/2000 | Scott |
| 6,127,560 A | 10/2000 | Stidham et al. |
| 6,175,037 B1 | 1/2001 | Tweedy |
| 6,291,712 B1 | 9/2001 | Saihata et al. |
| 6,319,187 B1 | 11/2001 | Scott |
| 6,365,885 B1 * | 4/2002 | Roy et al. ..................... 219/750 |
| 6,373,040 B2 | 4/2002 | Thomas |
| 6,614,010 B2 | 9/2003 | Fagrell et al. |
| 6,794,510 B2 | 9/2004 | Le Bourdonnec et al. |
| 6,867,400 B2 | 3/2005 | Collins et al. |
| 6,960,627 B2 | 11/2005 | Huth et al. |
| 6,989,519 B2 | 1/2006 | Collins, Jr. et al. |
| 7,150,836 B2 | 12/2006 | Meikrantz |
| 7,393,920 B2 | 7/2008 | Collins et al. |
| 7,473,739 B2 | 1/2009 | Dairoku et al. |
| 7,759,454 B2 | 7/2010 | Falk et al. |
| 8,067,635 B2 * | 11/2011 | Krull et al. ..................... 564/139 |
| 2003/0021793 A1 | 1/2003 | Hilgers |
| 2003/0091487 A1 * | 5/2003 | Fagrell .......................... 422/198 |
| 2005/0027120 A1 | 2/2005 | Gojon-Zorilla |
| 2005/0272631 A1 | 12/2005 | Miracle et al. |
| 2005/0274065 A1 | 12/2005 | Portnoff et al. |
| 2005/0283011 A1 | 12/2005 | Hoong et al. |
| 2006/0057482 A1 | 3/2006 | Yuasa |
| 2006/0228088 A1 | 10/2006 | Charlier de Chily et al. |
| 2006/0252884 A1 | 11/2006 | Falk et al. |
| 2006/0291827 A1 | 12/2006 | Suib et al. |
| 2007/0049721 A1 | 3/2007 | Nefzger et al. |
| 2007/0060762 A1 | 3/2007 | Kawashima et al. |
| 2008/0009541 A1 | 1/2008 | Chambers et al. |
| 2008/0202982 A1 | 8/2008 | Tooley |
| 2008/0264934 A1 | 10/2008 | Moreira et al. |
| 2010/0010244 A1 | 1/2010 | Krull et al. |
| 2010/0032284 A1 | 2/2010 | Krull et al. |
| 2010/0076040 A1 | 3/2010 | Krull et al. |
| 2010/0116642 A1 | 5/2010 | Krull et al. |
| 2010/0173107 A1 | 7/2010 | Hahn et al. |
| 2011/0083956 A1 | 4/2011 | Krull et al. |
| 2011/0083957 A1 | 4/2011 | Krull et al. |
| 2011/0089019 A1 | 4/2011 | Krull et al. |
| 2011/0089020 A1 | 4/2011 | Krull et al. |
| 2011/0089021 A1 | 4/2011 | Krull et al. |
| 2011/0092722 A1 | 4/2011 | Krull et al. |
| 2011/0137081 A1 | 6/2011 | Krull et al. |
| 2012/0088918 A1 | 4/2012 | Krull et al. |
| 2012/0090983 A1 | 4/2012 | Krull et al. |
| 2012/0095220 A1 | 4/2012 | Krull et al. |
| 2012/0095238 A1 | 4/2012 | Krull et al. |
| 2012/0103790 A1 | 5/2012 | Krull et al. |
| 2012/0178951 A1 | 7/2012 | Krull et al. |
| 2012/0184758 A1 * | 7/2012 | Krull et al. ..................... 554/167 |
| 2013/0274368 A1 | 10/2013 | Krull et al. |
| 2013/0289206 A1 | 10/2013 | Krull et al. |
| 2013/0296457 A1 | 11/2013 | Krull et al. |
| 2013/0296458 A1 | 11/2013 | Krull et al. |

FOREIGN PATENT DOCUMENTS

| | | |
|---|---|---|
| CN | 1351954 | 6/2002 |
| CN | 1749279 | 3/2006 |
| CN | 1931980 | 3/2007 |
| DE | 480866 | 8/1929 |
| DE | 1139738 | 11/1962 |
| DE | 2009156 | 7/1970 |
| DE | 2620638 | 11/1977 |
| DE | 3209800 | 9/1983 |
| DE | 224203 | 7/1985 |
| DE | 102005051637 | 5/2007 |
| DE | 102006047619 | 5/2010 |
| DE | 102009001382 | 9/2010 |
| EP | 0134995 | 3/1985 |
| EP | 0207901 | 1/1987 |
| EP | 0226501 | 6/1987 |
| EP | 0383605 | 8/1990 |
| EP | 0437480 | 7/1991 |
| EP | 0722994 | 7/1996 |
| EP | 0377177 | 7/1997 |
| EP | 0884305 | 12/1998 |
| EP | 1256565 | 11/2002 |
| EP | 1291077 A2 * | 3/2003 |
| EP | 1435364 | 7/2004 |
| EP | 1491552 | 12/2004 |
| EP | 1712543 | 10/2006 |
| EP | 1775311 | 4/2007 |
| EP | 2079762 | 6/2007 |
| EP | 1849854 | 10/2007 |
| EP | 1884559 | 2/2008 |

(56) References Cited

FOREIGN PATENT DOCUMENTS

| | | |
|---|---|---|
| GB | 0385978 | 3/1931 |
| GB | 0414366 | 7/1934 |
| GB | 0719792 | 12/1954 |
| GB | 2094806 | 9/1982 |
| GB | 2095262 | 9/1982 |
| GB | 2361918 | 11/2001 |
| JP | 10330338 | 5/1997 |
| JP | 11508873 | 8/1999 |
| JP | 2003321427 | 11/2003 |
| JP | 2005322582 | 5/2004 |
| JP | 2006181533 | 12/2004 |
| JP | 2005060256 | 3/2005 |
| JP | 2006272055 | 3/2005 |
| JP | 2008031082 | 2/2008 |
| JP | 2009263497 | 11/2009 |
| WO | WO 90/03840 | 4/1990 |
| WO | WO 94/18243 | 8/1994 |
| WO | WO 95/06518 | 3/1995 |
| WO | WO 95/09821 | 4/1995 |
| WO | WO 96/14344 | 7/1996 |
| WO | WO 98/29461 | 7/1998 |
| WO | WO 98/29467 | 7/1998 |
| WO | WO 98/39370 | 9/1998 |
| WO | WO 03/014272 | 2/2003 |
| WO | WO 03/016359 | 2/2003 |
| WO | WO 03/090669 | 11/2003 |
| WO | WO 2004/054707 | 7/2004 |
| WO | WO 2004/072031 | 8/2004 |
| WO | WO 2005/033062 | 4/2005 |
| WO | WO 2005/118526 | 12/2005 |
| WO | WO 2006/024167 | 3/2006 |
| WO | WO 2007/065681 | 6/2007 |
| WO | WO 2007/110384 | 10/2007 |
| WO | WO 2007/126166 | 11/2007 |
| WO | WO 2008/043492 | 4/2008 |
| WO | WO 2008/043493 | 4/2008 |
| WO | WO 2008/043494 A1 * | 4/2008 |
| WO | WO 2008/043495 | 4/2008 |
| WO | WO 2009/002880 | 12/2008 |
| WO | WO 2009/064501 | 5/2009 |
| WO | WO 2009/121490 | 10/2009 |

OTHER PUBLICATIONS

International Search Report for PCT/EP2007/008681 Mail dated Jan. 29, 2008.
Translation of International Preliminary Report on Patentability for PCT/EP2007/008681, Jan. 29, 2008.
International Search Report for PCT/EP2007/008680 Mail dated Feb. 15, 2008.
Translation of International Preliminary Report on Patentability for PCT/EP2007/008680, Feb. 15, 2008.
International Search Report for PCT/EP2007/008679 Mail dated Feb. 4, 2008.
International Search Report for PCT/EP2007/008678 Mail dated Mar. 10, 2008.
Translation of International Preliminary Report on Patentability for PCT/EP2007/008678, Mar. 10, 2008.
International Search Report for PCT/EP2007/008677 Mail dated Mar. 3, 2008.
Translation of International Preliminary Report on Patentability for PCT/EP2007/008677, Mar. 3, 2008.
International Search Report for PCT/EP2009/001989 mail dated Jun. 10, 2009.
Translation of International Preliminary Report on Patentability for PCT/EP2009/001989, dated Oct. 14, 2010.
International Search Report for PCT/EP2009/001985 mail dated Jun. 10, 2009.
Translation of International Preliminary Report on Patentability for PCT/EP2009/001985, dated Oct. 14, 2010.
International Search Report for PCT/EP2009/001986 mail dated Jun. 18, 2009.
Translation of International Preliminary Report on Patentability for PCT/EP2009/001986, Oct. 14, 2010.
International Search Report for PCT/EP2009/001987 mail dated Jun. 10, 2009.
Translation of International Preliminary Report on Patentability for PCT/EP2009/001987, dated Oct. 14, 2010.
International Search Report for PCT/EP2009/001984 mail dated Jun. 10, 2009.
Translation of International Preliminary Report on Patentability for PCT/EP2009/001984, dated Oct. 14, 2010.
International Search Report for PCT/EP2009/001990 mail dated Jun. 10, 2009.
Translation of International Preliminary Report on Patentability for PCT/EP2009/001990, dated Dec. 9, 2010.
International Search Report for PCT/EP2009/001988 mail dated Jul. 9, 2009.
Translation of International Preliminary Report on Patentability for PCT/EP2009/001988, dated Jan. 27, 2011.
International Search Report for PCT/EP2010/003446 mail dated Feb. 9, 2011.
Translation of International Preliminary Report on Patentability for PCT/EP2010/003446, dated Jan. 19, 2012.
International Search Report for PCT/EP2010/003447 mail dated Feb. 9, 2011.
Translation of International Preliminary Report on Patentability for PCT/EP2010/003447, dated Feb. 9, 2012.
Written Opinion of the IPEA for PCT/EP2010/003447, dated Sep. 9, 2011.
International Search Report for PCT/EP2010/003444 mail dated Feb. 9, 2011.
Translation of International Preliminary Report on Patentability for PCT/EP2010/003444, dated Jan. 19, 2012.
Response to the Written Opinion in PCT/EP2010/003444, dated Sep. 9, 2011.
International Search Report for PCT/EP2010/003445 mail dated Sep. 1, 2010.
Translation of International Preliminary Report on Patentability for PCT/EP2010/003445, dated Jan. 5, 2012.
International Search Report for PCT/EP2010/003442 mail dated Jul. 20, 2010.
Translation of International Preliminary Report on Patentability for PCT/EP2010/003442, dated Feb. 16, 2012.
International Search Report for PCT/EP2010/003443 mail dated Feb. 9, 2011.
Translation of International Preliminary Report on Patentability for PCT/EP2010/003443, dated Feb. 16, 2012.
International Search Report for PCT/EP2010/005427 dated Mar. 21, 2011.
Translation of International Preliminary Report on Patentability for PCT/EP2010/005427, dated Mar. 21, 2011.
International Search Report for PCT/EP2010/005428 dated Jan. 27, 2011.
Translation of International Preliminary Report on Patentability for PCT/EP2010/005428, dated Jan. 27, 2011.
International Search Report for PCT/EP2011/006173 mail dated May 8, 2012.
Translation of International Preliminary Report on Patentability for PCT/EP2011/006173, dated Jul. 4, 2013.
International Search Report for PCT/EP2011/006172 mail dated Jul. 10, 2012.
Translation of International Preliminary Report on Patentability for PCT/EP2011/006172, dated Jul. 4, 2013.
International Search Report for PCT/EP2011/006175 mail dated May 9, 2012.
Translation of International Preliminary Report on Patentability for PCT/EP2011/006175, dated Jul. 4, 2013.
International Search Report for PCT/EP2011/006174 mail dated Jul. 10, 2012.
Translation of International Preliminary Report on Patentability for PCT/EP2011/006174, dated Jul. 4, 2013.
International Search Report for PCT/EP2011/006176 mail dated Aug. 1, 2012.

(56) References Cited

OTHER PUBLICATIONS

Translation of International Preliminary Report on Patentability for PCT/EP2011/006176, dated Jul. 4, 2013.
"Fatty Acids and Chemical Specialties", pp. 131-147, 1955.
"Microwave Synthesis" by B. L. Hayes, CEM Publishing 2002.
"Microwave vs. Conventional Heating", webpage, www.biotage.com, Jan. 2009.
"Objective Colour Assesment and Quality Control in the Chemical, Pharmaceutical and Cosmetic Industries", Application Report No. 3.9 e from Hach Lange, pp. 1-28, Feb. 2013.
Hawley's Condensed Chemical Dictionary, 14th ed., Lewis, Richard J. Sr. ed., copyright 2002 John Wiley & Sons, Inc., available online at http://www.knovel.comiwebiportalibrowseidisplay? EXT KNOVEL DISPLAY bookid=704&VerticalID=0.
A. Breccia et al, "Reaction Between Methanol And Commercial Seed Oils Under Microwave Irradiation" Internation Microwave Power Institute 1999, 34, pp. 3-8.
Advanced Organic Chemistry: Reactions, Mechanisms, and Structure; Second Edition, Jerry March, Wiley-Interscience Publication, pp. 324-331 and 382-389, 1977.
Amore et al. (Macromolecular Rapid Communications, vol. 28 (2007), Issue 4, pp. 473-477).
An et al. (J. Org. Chem. (1997), 62, 2505-2511).
Wolf, et al., AOSTRA Journal of Research 3 (1986) "Microwave Assisted Catalytic Conversion of Cyclohesxene" pp. 53-59.
Arfan et al, "Efficient Combination of Recyclable Task Specific Ionic Liquid and Microwave Dielectric Heating for the Synthesis of Lipophilic Esters," Organic Process Research & Development vol. 9, pp. 743-748 (2005).
B. Toukoniitty, et al: "Esterification of propionic acid under microwave irradiation over an ion-exchange resin", Catalysis Today, Elsevier, NL, vol. 100, No. 3-4, Feb. 28, 2005, pp. 431-435, XP004850051.
Barbosa et al, "Niobium to alcohol mol ratio control of the concurring esterification and etherification reactions promoted by NbCl5 and Al2O3 catalysts under microwave irradiation," App. Catalysis A: General vol. 338, pp. 9-13 (2008).
Beilstein Substance Identification, BRN No. 6190607, 1981.
Bose et al, "Microwave promoted energy-efficient N-Formylation with aqueous formic acid," Tetrahedron Let. vol. 47 (2006), pp. 4605-4607.
C. Ferroud, et al: "Microwaves-assisted solvent-free synthesis of N-acetamides by amidation or aminolysis", Tetrahedron Letters., vol. 49, Mar. 6, 2008, pp. 3004-3008, XP022602751 NL Elsevier, Amsterdam.
C. Mazzocchia et al., "Fatty acid methyl esters synthesis from triglycerides over heterogeneous catalysts in the presence of microwaves" C.R. Chimie 7 (2004) pp. 601-605.
C. Chen et al., J. Chem. Soc., Chem. Commun., 1990, 807-809.
Chemat, et al: "The role selective heating in the microwave activation of heterogeneous catalysis reactions using a continuous microwave reactor", Journal of Microwave Power and Electromagnetic Energy, The Institute, Vienna, VA, US, vol. 33, No. 2, Jan. 1, 1998, pp. 88-94, XP009143773.
D. Bogdal, Microwave-assisted Organic Synthesis, Elsevier 2005.
Desai et al, "Thermal and microwave-assisted N-formylation using solid-supported reagents," Tetrahedron Let. vol. 46 (2005), pp. 955-957.
DiLuca et al, "A new, simple procedure for the synthesis of formyl amides," Synlett No. 14 (2004), pp. 2570-257.
Ella Bezdushna et al. Macromolecular Chemistry & Physics, vol. 209, pp. 1942-1947, XP55023715, 2008.
Ella Bezoushna et al: "Microwave Assisted Esterification of Methacrylic Acid and Polymer-Analogous Esterification of Poly[ethylene-co-(acrylic acid)] with Dissimilar Phenols", Macromolecular Rapid Communications, vol. 208, No. 4, Feb. 19, 2007, pp. 443-448, XP55023715.
Energieeintrag im Discover, "Flexibilitaet ist Trumpf", http://www.cem.de/documents/produlde/mikro_synthese/allgemeines/flexibel.htm, Jun. 2009.

English Abstract for CH 681586, Apr. 15, 1993.
English Abstract for CN 1749279, Mar. 2006.
English Abstract for CN 1931980, Mar. 2007.
English Abstract for DD 224203, Jul. 3, 1985.
English Abstract for DE 102005051637, May 3, 2007.
English Abstract for DE 102009001382, Sep. 9, 2010.
English Abstract for DE 2620638, Nov. 24, 1977.
English Abstract for DE 480866, Aug. 1929.
English Abstract for EP 0134995, Mar. 27, 1985.
English Abstract for EP 1256565, Nov. 13, 2002.
English Abstract for JP 10330338, May 1997.
English Abstract for JP 2003321427, Nov. 11, 2003.
English Abstract for JP 2005060256, Mar. 10, 2005.
English Abstract for JP 2005322582, May 2005.
English Abstract for JP 2006181533, Dec. 2004.
English Abstract for JP 2006272055, Mar. 2005.
English Abstract for JP 2006031082, Feb. 14, 2008.
English Abstract for JP 52125142, Oct. 20, 1977.
English Abstract for JP 54005931, Jan. 17, 1979.
English Abstract for WO 03/090869, Nov. 6, 2003.
English Translation of CN 1351954, Jun. 5, 2002.
English translation of DIN Standard 6162, Mar. 2013.
English translation of JP 2009 263 497, 2009.
Erik Esveld, et al: "Pilot Scale Continuous Microwave Dry-Media Reactor. Part 1: Design and Modeling", Chemical Engineering and Technology, Weinheim, DE, vol. 23, No. 3, Jan. 1, 2000, pp. 279-283, XP007916923.
Erik Esveld, et al: "Pilot Scale Continuous Microwave Dry-Media Reactor Part II: Application to Waxy Esters Production", Chemical Engineering and Technology, Weinheim, DE, vol. 23, No. 5, Jan. 1, 2000, pp. 429-435, XP007916803.
Fats and Oils: Formulating and Processing for Applications, Second Ed., O'Brien, CRC Press 2003, Ch. 3, sec. 3.4.2., lines 12-13.
Fatty Acids Division, Soap Association, "Fatty Acids for Chemical Specialties: A symposium of the Soap, Detergents, and Sanitary Chemical Products Division of the Chemical Specialties Manufacturers Association," 1955, pp. 131-147, available online at http://www.aciscience.org/Oleochemical/FattyAcid.aspx.
G. Pipus, et al: "Esterification of benzoic acid in microwave tubular flow reactor", Chemical Engineering Journal, Elsevier Sequoia, Lausanne, CH, vol. 76, Jan. 1, 2000, pp. 239-245, XP007916929.
Gelens et al., Tetrahedron Letters 2005, 46(21), 3751-3754.
Glasnov, et al: "Microwave-assisted synthesis under continuous-flow conditions", Macromolecular Rapid Communications, 28(4), 395-410 Coden: MRCOE3; Jan. 1, 2007, XP002529633.
Gonzalez et al, "Tartradiamide formation by thermolysis of tartaric acid with alkylamines," Tetrahedron Letters vol. 49 (2008 3925-3926.
Gorelzki et al., Macromol. Rapid Commun. 2004, 25, 513-516.
H.J. Bauer, et al., Makromol. Chem., 183, 1982, pp. 2971-2976.
Iannelli et al., Tetrahedron 2005, 61, 1509-1515.
Ishihara et al, "3,4,5-Trifluorobenzeneboronic Acid as an Extremely Active Amidation Catalyst," J. Org. Chem. vol. 61, (1996), pp. 4196-4197.
J. Kremsner, et al, Top Curr Chem, (2006) 266: pp. 233-278.
J. Ruhoff, et al., J. Am. Chem. Soc., 59(1937), 401-402.
Jain et al, "Acetylation of some organic compounds under microwave irradiation," J. Indian Chem. Soc., vol. 84, Feb. 2007, p. 188.
K. Lange, K.H. Löcherer, Taschenbuch der Hochfrequenztechnik [Pocket book of high-frequency technology], vol. 2, p. K21 ff, Sep. 11, 2008.
Kangani, et al., "One Pot direct synthesis of amides or oxazolines from carboxylic acids using Deoxo-Fluor reagent," Tetrahedron Letters, vol. 46, (2005), pp. 8917-8920.
Karl G. Kempf et al: "A Procedure for Preparing Aryl Esters of Polyacids. The Conversion of Poly(methacrylic acid) to Poly(phenyl methacrylate)", Macromolecules, vol. 11, No. 5, Sep. 1, 1978, pp. 1038-1041, XP55024162.
Katritzky et al. (Energy & Fuels 4 (1990), 555-561).
KIC Chemicals Inc., Capric Acid, available online at http://www.kicgroup.com/capric.htm, Jan. 30, 2003.
Konrad G. Kabza, et al: "Microwave-Induced Esterification Using Heterogeneous Acid Catalyst in a Low Dielectric Constant Medium",

(56) References Cited

OTHER PUBLICATIONS

Journal of Organic Chemistry, American Chemical Society, Easton.; US, vol. 65, Jan. 1, 2000, pp. 1210-1214, XP007916930.

Kumar, et al, "Microwave Assisted Direct Synthesis of 2-Substituted Benzoxazoles From Carboxylic Acids Under Catalyst and Solvent-Free Conditions", Synlett, No. 9, 2005, pp. 1401-1404.

L. Perreux, et al: "Microwave effects in solvent-free esters aminolysis" Tetrahedron, Elsevier Science Publishers, Amsterdam, NL, vol. 59, No. 12, Mar. 17, 2003, pp. 2185-2189, XP004414169.

L. Perreux, et al: "Solvent-free preparation of amides from acids and primary amines under microwave irradiation", Tetrahedron, Elsevier Science Publishers, Amsterdam, NL, vol. 58, No. 11, Mar. 11, 2002, pp. 2155-2162, XP004343866.

Leadbeater, et al, Continuous-Flow Preparation of Biodiesel Using Microwave Heating:, Energy & Fuels 2007, 21, pp. 1777-1781.

M. Hajek in A. Loupe "Microwaves in Organic Synthesis", Wiley, 2006, Chapter 13, pp. 615-652.

M. S. Nery, et al., "Niobium pentachloride promoted conversion of carboxylic acids to carboxamides: Synthesis of the 4-aryl-1,2,3,4-tetrahydrolsoquinollne alkaloid structures" Synthesis, (2),272-276, 2003.

Machetti, et al, "Parallel Synthesis of an Amide Library Based on the 6,8-Dioxa-3-azabicyclo[3.2.1.]octane Scaffold by Direct Aminolysis of Methyl Esters," J. Comb. Chem., 2007, vol. 9, pp. 454-461.

Massicot et al, Synthesis 2001 (16), 2441-2444.

Mazzocchia, C., et al., Fast synthesis of biodiesel from trigycerides in presence of microwave, 2006, Advances in Microwave and Radio Frequency Processing, Report of the 8th international conference on microwave and high frequency heatting held in Bayrueth, Germany, Sep. 2001, Springer Berlin Heidelberg, Part V, pp. 370-376 (18 pages).

Mohan et al, "Zeolite catalyzed acylation of alcohols and amines with acetic acid under microwave irradiation," Green Chem. 2006, vol. 8, pp. 368-372.

N. Azcan et al, "Alkali catalyzed transesterification of cottonseed oil by microwave irradiation" Fuel 86 (2007) pp. 2639-2644, XP022322088.

N. Azcan et al, "Microwave assisted transesterification of rapeseed oil" Fuel 87 (2008) pp. 1781-1788, XP022611169.

N. Leadbeater et al, "Fast, Easy Preparation of Biodiesel Using Microwave Heating" Energy & Fuels 2006, 20, pp. 2281-2283.

N. Saifuddin et al, "Production Of Ethyl Ester (Biodiesel) from used Frying Oil: Optimization of Transesterification Process using Microwave Irradiation" Malaysian Journal of Chemistry, 2004, vol. 6, pp. 77-82.

Noel S. Wilson, et al: "Development and Applications of a Practical Continuous Flow Microwave Cell", Organic Process Research and Development, American Chemical Society, US, vol. 8, No. 3, Jan. 1, 2004, pp. 535-538, XP007916928.

Oliver Kretschmann et al: Microwave-Assisted Synthesis of Associative Hydrogels., Macromolecular Rapid Communications, vol. 28, No. 11, Jun. 1, 2007, pp. 1265-1269, XP55023774.

Pipus et al. (First European Congress on Chemical Egineering, Firenze, Italy, May 4-7, 1997: AIDIC: Milan, Italy, 1997: pp. 45-48).

Pollington, Journal of Organic Chemistry, vol. 56, pp. 1313-1314, 1991.

Q. Yang et al. (Synth. Commun. 2008, 38, 4107-4115).

R. Jachuck, et al: "Process intensification: oxidation of benzyl alcohol using a continuous isothermal reactor under microwave irradiation", Green Chemistry, Royal Society of Chemistry, Cambridge, GB, vol. 8, Jan. 1, 2006, pp. 29-33, XP007916789.

R. Martinez-Palou, et al., "Synthesis of Long Chain 2-Alkyl-1-(2-hydroxyethyl)-2-imidazolines Under Microwave in Solvent-Free Conditions", Synlett 2003, No. 12, pp. 1847-1849.

R. Plantier-Royon, et al., "Synthesis of Functionalized Bis-Amides of L-(+)-Tartaric Acid and Application as Copper(II) Ligands", C.R. Chimie, 2004, pp. 119-123.

R. S. Varma, et al: "Solvent-free synthesis of amides from non-enolizable esters and amines using microwave irradiation" Tetrahedron Letters, Elsevier, Amsterdam, NL, vol. 40, No. 34, Aug. 20, 1999, pp. 6177-6180, XP004174006.

R.S. Hunter, "Conversion of Visual to Instrumental Measurements of Yellowness", 1981, JAOCS, May, pp. 606-612.

Reddy et al, "Zirconyl chloride promoted highly efficient solid phase synthesis of amide derivatives," Chinese Chemical Letters, vol. 18 (2007), pp. 1213-1217.

S. Schmitz, et al., "Access to Poly(N-[3-(dimethylamino)propyl](meth)acrylamide) via Microwave-Assisted Synthesis and Control of LCST-Behavior in Water", Macromolecular Rapid Communications, vol. 28, No. 21, Nov. 1, 2007, pp. 2080-2083.

Sebastian Sinnwell et al: "Microwave assited hydroxyalkylamidation of poly(ethylene-co-acrylic acid) and formation of grafted poly([epsilon]-caprolactone) side chains", Journal of Polymer Science Part A: Polymer Chemistry, vol. 45, No. 16, Aug. 15, 2007, pp. 3659-3667, XP55024233.

Shore, et al, "Catalysis in Capillaries by Pd Thin Films Using Microwave-Assisted Continuous-Flow Organic Synthesis (MACOS)" Angewandte Chemie 2006, 118, pp. 2827-2832.

Synthewave 402 Manual, 2000, Prolabo, Support pages (2) and Manual pp. 1-13 (total 15 pages).

T. Cablewski, et al: "Development And Application Of A Continuous Microwave Reactor For Organic Synthesis" Journal of Organic Chemistry, American Chemical Society, Easton.; US, vol. 59, Jan. 1, 1994, pp. 3408-3412, XP000198783.

Translation of SIPO Office Action for Application 200980101830.0, May 12, 2012.

Translation of SIPO Search Report for Application 200980101830.0, May 12, 2012.

V. Lertsathapomsuk et al, "Microwave assisted in continuous biodiesel production from waste frying palm oil and its performance in a 100 kW diesel generator" Fuel Processing Technology 89 (2008) pp. 1330-1336, XP025681095.

Vacek et al, "Selective enzymic esterification of free fatty acids with n-butanol under microwave irradiation and under classical heating," Biotechnology Letters, vol. 22, pp. 1565-1570 (2000).

Vazquez-Tato, M.P., "Microwave-Mediated Synthesis of Amides", Synlett, No. 7, 1993, p. 506.

X. Wu, et al., "Microwave Enhanced Aminocarbonylations in Water", Organic Letters, 7(15), pp. 3327-3329, 2005.

Zhaoju Yu et al: "Biodegradable polyvinyl alcohol)-graftpoly(epsilon-caprolactone) comb-like polyester: Microwave synthesis and its characterization", Journal of Applied Polymer Science, vol. 104, No. 6, Jun. 15, 2007, pp. 3973-3979, XP55023817, Aug. 22, 2001.

Zradni et al. (Synth. Commun. 2002, 32, 3525-3531).

Zradni, et al, "Minutes Synthesis of Amides from Esters and Amines Under Microwave Irradiation," Fifth International Electronic Conference on Synthetic Organic Chemistry (ECSOC-5), available at http://www.mdpi.org/ecsoc/ecsoc-5/Papers/e0013/e0013.html.

Arora et al, "A mild and efficient procedure for the conversion of aromatic carboxylic acid esters to secondary amides" Can. J. Chem, vol. 83 (2005), pp. 1137-1140.

Essen et al, "The Velocity of Propagation of Electromagnetic Waves Derived from the Resonant Frequencies of a Cylindrical Cavity Resonator," Proc. R. Soc. Lond. A (1948), vol. 194, pp. 348-361.

Katritzky et al, "Efficient microwave access to polysubstituted amidines from imidoylbenzotriazoles," J. Org. Chem. vol. 71, pp. 3375-3380 (2006).

Petricci et al, "Microwave-assisted acylation of amines, alcohols, and phenols by the use of solid-supported reagents (SSRs)," J. Org. Chem. vol. 69, pp. 7880-7887, (2004).

Werner et al, "Design and synthesis of a 3,4-dehydroproline amide discovery library," J. Comb. Chem. (2007), 9(4), pp. 677-683.

* cited by examiner

DEVICE FOR CONTINUOUSLY CARRYING OUT CHEMICAL REACTIONS AT HIGH TEMPERATURES

Priority is claimed as a national stage application, under 35 U.S.C. § 371, to PCT/EP2010/003443 filed on Jun. 9, 2010, now WO 2011/000460, which claims priority to DE 10 2009 031 059.2, filed Jun. 30, 2009. The disclosures of the aforementioned priority application are incorporated by reference in their entirety.

The present invention relates to an apparatus for continuously performing chemical reactions at high temperatures and elevated pressure with heating by microwave irradiation on the industrial scale.

Chemical reactions can be accelerated by increasing the temperature. However, the temperature increase in industrial processes is limited by the pressures which then arise. At least in large reaction vessels of several liters or several cubic meters, the performance of reactions under high pressures, due to the safety risks which then occur, is achievable only with a high level of technical complexity, if at all. Furthermore, reactions conducted in conventional stirred vessels, for example in Pfaudler tanks, require correspondingly higher jacket or else heating element temperatures to establish the reaction temperature, in order to ensure the heat transfer required. However, this results in local overheating at the heating surfaces and in many cases also in unwanted side reactions, or else decomposition of the reaction mixture, which leads to reduced product quality and/or reduced yields.

Although the safety risks caused by high pressures can be reduced by the use of continuous reaction tubes, the problems caused by the temperature gradients required in the transfer of heat to the reaction medium exist here too. For rapid heating rates, high jacket temperatures are required, which can in turn lead to unwanted side reactions or even decompositions. Moderate jacket temperatures, in contrast, require long residence times in the reaction tube to attain the target temperature, and hence low flow rates and/or long tubes. During this gradual heating, unwanted side reactions are likewise observed in many reactions.

A more recent approach for chemical synthesis is the performance of reactions in a microwave field. This reaction technique has been employed to date mainly on the laboratory scale and only rarely on the small pilot plant scale, since there have been no known apparatuses to date which enable the production of more than a few kg per day.

WO-90/03840 discloses a continuous process for performing various chemical reactions in a continuous laboratory microwave reactor. The reaction mixture is heated to temperatures of up to 190° C. with variable flow rates of up to 1.4 l/h in a multimode microwave oven under pressures of up to 12 bar. Essentially immediately after passing through the microwave zone, the reaction product is cooled. In many cases, however, the conversions achieved still exhibit potential for optimization, and the efficiency of this process with regard to the microwave absorption of the reaction mixture is low due to the more or less homogeneous distribution of microwave energy over the applicator space in multimode microwave applicators and the lack of focus on the tube coil. A significant increase in the incident microwave power would lead here to unwanted plasma discharges. Furthermore, the spatial inhomogeneities of the microwave field which change with time and are referred to as hotspots make a reliable and reproducible reaction regime on a large scale impossible.

EP-A-1 291 077 discloses a microwave reactor in which a liquid in a tube is conducted through a microwave hollow conductor transverse to the direction of propagation of the standing electromagnetic wave, and in which molecules are activated by dissociation and/or ionization by means of microwave radiation, in order subsequently to be reacted with further reactants in a reaction space. Due to the very small irradiation zone, the amount of substance which can be treated therein is firstly extremely limited, and the amount of energy which can be introduced is secondly low. Upscaling of this process by increasing the tube cross section is additionally opposed by the penetration depth of microwaves into the reaction mixture, which is typically limited to a few millimeters to a few centimeters.

Esveld et al., Chem. Eng. Technol. 23 (2000), 429-435, disclose a continuous process for preparing wax esters, in which fatty alcohol and fatty acid are esterified without solvent in the presence of montmorillonite. On a conveyor belt, the reaction mixture is heated to reaction temperature by microwave radiation within 5 minutes and then held at this temperature for a further 30 minutes for substantial removal of the water of reaction formed. This process performed in an open system is by its nature applicable only to high-boiling reactants (and reaction products).

Typically, the reaction mixture, in the case of microwave-supported reactions performed continuously in a flow tube, is cooled as rapidly as possible immediately after leaving the irradiation zone, for example by adiabatic expansion according to WO-04/054707.

Many chemical reactions require not only rapid and controlled heating to establish the chemical equilibrium and hence to optimize the yield, but also a certain residence time at the target reaction temperature. Therefore, to establish the chemical equilibrium and hence to achieve maximum yields, an appropriate residence time in the microwave irradiation zone would be desirable, but this reduces the throughput and hence the space-time yield.

It was accordingly an object of the invention to provide an apparatus for continuous performance of chemical reactions on the industrial scale at high temperatures, in which the reaction mixture can be heated to the desired reaction temperature very rapidly and without partial overheating and then held at this reaction temperature for a defined period and subsequently cooled. In addition, the apparatus should allow operation above atmospheric pressure, such that all components of the reaction mixture remain in the liquid state. The apparatus should enable a high space-time yield, a high energetic efficiency and additionally safe and reproducible operation.

It has been found that, surprisingly, chemical reactions can be performed particularly gently and with very high space-time yields in an apparatus in which the reaction mixture in a microwave-transparent tube is conducted through a heating zone in which it is heated to reaction temperature within a very short time by means of microwaves and from which the heated and optionally pressurized reaction mixture is transferred into an isothermal reaction zone, and after leaving the latter it is optionally decompressed and cooled.

The invention provides an apparatus for continuously performing chemical reactions, comprising a microwave generator, a microwave applicator with a microwave-transparent tube within, and an isothermal reaction zone, which are arranged such that the reaction mixture in the microwave-transparent tube is conducted through a microwave applicator which functions as a heating zone, within which it is heated to reaction temperature by means of microwaves which are conducted out of the microwave generator into the microwave applicator, and within which the heated and optionally pressurized reaction mixture is transferred immediately after leaving the heating zone into an isothermal reaction zone adjoining the heating zone and, after leaving the isothermal reaction zone, is cooled.

The invention further provides a process for continuously performing chemical reactions, in which the reaction mixture, in a microwave-transparent tube, is conducted through a heating zone in which it is heated to reaction temperature by means of microwaves and in which the heated and optionally pressurized reaction mixture is transferred immediately after leaving the heating zone into an isothermal reaction zone adjoining the heating zone and, after leaving the isothermal reaction zone, is cooled.

The inventive apparatus and the inventive process are preferably suitable for those reactions which require a certain activation energy. They are especially suitable for reactions whose activation energy is at least 0.01 kJ/mol, preferably at least 0.1 kJ/mol, for example 1 to 100 kJ/mol. Additionally preferably, the inventive apparatus and the inventive process are suitable for reactions which proceed without significant exothermicity. For instance, they are especially suitable for reactions whose exothermicity ΔH is less than −20 kJ/mol and especially less than −10 kJ/mol, for example less than −2 kJ/mol. The inventive apparatus and the inventive process are especially preferred for endothermic reactions whose exothermicity ΔH is greater than +0.1 kJ/mol and especially between +1 kJ/mol and +100 kJ/mol, for example between +2 kJ/mol and 70 kJ/mol. Examples of suitable chemical reactions are esterifications, amidations, ester hydrolyses, etherifications, acetalizations, ene reactions, Diels-Alder reactions, oxidations, reductions, hydrogenations, nucleophilic substitutions, additions, hydrolyses, isomerizations, condensations, decarboxylations, eliminations and polymerizations, for example polycondensations. In addition to the actual reactants, the reaction mixtures may also comprise assistants, for example solvents and/or catalysts, to accelerate the reactions.

Microwaves refer to electromagnetic rays with a wavelength between about 1 cm and 1 m and frequencies between about 300 MHz and 30 GHz. This frequency range is suitable in principle for the process according to the invention. Preference is given in accordance with the invention to using microwave radiation with the frequencies approved for industrial, scientific, medical, domestic or similar applications, for example frequencies of 915 MHz, 2.45 GHz, 5.8 GHz or 24.12 GHz.

In a preferred embodiment, the inventive apparatus comprises, as the microwave-transparent tube, a pressure-resistant, chemically inert tube (heating tube), the reaction mixture being exposed to the microwave radiation as it flows through said tube. For the microwave irradiation, it is possible to use multimode or else monomode microwave ovens (or microwave applicators) of different geometries.

Microwave generator, microwave applicator and microwave-transparent tube are arranged such that the reaction mixture in the microwave-transparent tube is conducted through a microwave applicator which functions as a heating zone, in which it is heated to reaction temperature by means of microwaves which are conducted out of the microwave generator into the microwave applicator. The isothermal reaction zone is arranged such that the heated and optionally pressurized reaction mixture passes immediately after leaving the heating zone into the isothermal reaction zone adjoining the heating zone and, after leaving the isothermal reaction zone, is cooled.

The heating tube may, for example, be straight or else in the form of a tube coil. For example, in multimode microwave ovens, the use of tube coils as the heating tube has been found to be particularly useful. In addition, in monomode microwave ovens, the use of straight tubes as the heating tube has been found to be particularly useful. In a particularly preferred embodiment, the reaction mixture is heated in a microwave-transparent, straight tube, the longitudinal axis of which is in the direction of propagation of the microwaves of a monomode microwave applicator.

The reaction mixture is preferably irradiated with microwaves in a microwave-transparent, straight heating tube within a hollow conductor connected to a microwave generator. The heating tube is preferably aligned axially with the central axis of symmetry of the hollow conductor.

The hollow conductor which functions as the microwave applicator is preferably configured as a cavity resonator. Additionally preferably, the microwaves unabsorbed by the reaction mixture in the hollow conductor are reflected at the end thereof. The length of the cavity resonator is preferably such that a standing wave forms therein. Configuration of the microwave applicator as a resonator of the reflection type achieves a local increase in the electrical field strength in the applicator at the same power supplied by the generator and increased energy exploitation.

The cavity resonator is preferably operated in $E_{01n}$ mode where n is an integer and specifies the number of field maxima of the microwave along the central axis of symmetry of the resonator. In this operation, the electrical field is directed in the direction of the central axis of symmetry of the cavity resonator. It has a maximum in the region of the central axis of symmetry and decreases to the value 0 toward the outer surface. This field configuration is rotationally symmetric about the central axis of symmetry. Use of a cavity resonator with a length where n is an integer enables the formation of a standing wave. According to the desired flow rate of the reaction mixture through the heating tube, the temperature desired and the residence time required therefor in the resonator, the length of the resonator is selected relative to the wavelength of the microwave radiation used. n is preferably an integer from 1 to 200, more preferably from 2 to 100, particularly from 3 to 50, especially from 4 to 20, for example three, four, five, six, seven, eight, nine or ten. The $E_{01n}$ mode of the cavity resonators is also referred to in English as the $TM_{01n}$ mode; see, for example, K. Lange, K. H. Löcherer, "Taschenbuch der Hochfrequenztechnik" [Handbook of High-Frequency Technology], volume 2, pages K21 ff.

The microwave energy can be injected into the hollow conductor which functions as the microwave applicator through holes or slots of suitable dimensions. In an embodiment particularly preferred in accordance with the invention, the reaction mixture is irradiated with microwaves in a heating tube present in a hollow conductor with a coaxial transition of the microwaves. Microwave devices particularly preferred for this process are formed from a cavity resonator, a coupling device for injecting a microwave field into the cavity resonator and with one orifice each on two opposite end walls for passage of the reaction tube through the resonator. The microwaves are preferably injected into the cavity resonator by means of a coupling pin which projects into the cavity resonator. The coupling pin is preferably configured as a preferably metallic inner conductor tube which functions as a coupling antenna. In a particularly preferred embodiment, this coupling pin projects through one of the end orifices into the cavity resonator. The heating tube more preferably adjoins the inner conductor tube of the coaxial transition, and is especially conducted through the cavity thereof into the cavity resonator. The heating tube is preferably aligned axially with a central axis of symmetry of the cavity resonator. For this purpose, the cavity resonator preferably has one central orifice each on two opposite end walls for passage of the heating tube.

The microwaves can be fed into the coupling pin or into the inner conductor tube which functions as a coupling antenna, for example, by means of a coaxial connecting line. In a preferred embodiment, the microwave field is supplied to the resonator via a hollow conductor, in which case the end of the coupling pin projecting out of the cavity resonator is conducted into the hollow conductor through an orifice in the wall of the hollow conductor, and takes microwave energy from the hollow conductor and injects it into the resonator.

In a specific embodiment, the reaction mixture is irradiated with microwaves in a microwave-transparent heating tube which is axially symmetric within an $E_{01n}$ round hollow conductor with a coaxial transition of the microwaves. Preferably, the heating tube is conducted through the cavity of an inner conductor tube which functions as a coupling antenna into the cavity resonator. In a further preferred embodiment, the reaction mixture is irradiated with microwaves in a microwave-transparent reaction tube which is conducted through an $E_{01n}$ cavity resonator with coaxial introduction of the microwaves, the length of the cavity resonator being such as to form n=2 or more field maxima of the microwave. In a further preferred embodiment, the reaction mixture is irradiated with microwaves in a microwave-transparent reaction tube which is conducted through an $E_{01n}$ cavity resonator with axial introduction of the microwaves, the length of the cavity resonator being such as to form a standing wave where n=2 or more field maxima of the microwave. In a further preferred embodiment, the reaction mixture is irradiated with microwaves in a microwave-transparent heating tube which is axially symmetric within a circular cylindrical $E_{01n}$ cavity resonator with a coaxial transition of the microwaves, the length of the cavity resonator being such as to form n=2 or more field maxima of the microwave. In a further preferred embodiment, the reaction mixture is irradiated with microwaves in a microwave-transparent reaction tube which is axially symmetric within a circular cylindrical $E_{01n}$ cavity resonator with a coaxial transition of the microwaves, the length of the cavity resonator being such as to form a standing wave where n=2 or more field maxima of the microwave.

Microwave generators, for example the magnetron, the klystron and the gyrotron, are known to those skilled in the art.

The heating tubes used for microwave irradiation are preferably manufactured from microwave-transparent, high-melting material. Particular preference is given to using non-metallic heating tubes. "Microwave-transparent" is understood here to mean materials which themselves absorb a minimum amount of microwave energy and convert it to heat. A measure employed for the ability of a substance to absorb microwave energy and convert it to heat is often the dielectric loss factor $\tan \delta = \in''/\in'$. The dielectric loss factor $\tan \delta$ is defined as the ratio of dielectric loss $\in''$ to dielectric constant $\in'$. Examples of $\tan \delta$ values of different materials are reproduced, for example, in D. Bogdal, Microwave-assisted Organic Synthesis, Elsevier 2005. For reaction tubes suitable in accordance with the invention, materials with $\tan \delta$ values measured at 2.45 GHz and 25° C. of less than 0.01, particularly less than 0.005 and especially less than 0.001 are preferred. Preferred microwave-transparent and thermally stable materials include primarily mineral-based materials, for example quartz, aluminum oxide, sapphire, zirconium oxide, silicon nitride and the like. Other suitable tube materials are thermally stable plastics, such as especially fluoropolymers, for example Teflon, and industrial plastics such as polypropylene, or polyaryl ether ketones, for example glass fiber-reinforced polyetheretherketone (PEEK). In order to withstand the temperature conditions during the reaction, minerals, such as quartz or aluminum oxide, coated with these plastics have been found to be especially suitable as reactor materials.

Inventive heating tubes particularly suitable for the microwave irradiation have an internal diameter of one millimeter to approx. 50 cm, particularly between 2 mm and 35 cm, especially between 5 mm and 15 cm, for example between 10 mm and 7 cm. Heating tubes are understood here to mean vessels whose ratio of length to diameter is greater than 5, preferably between 10 and 100 000, more preferably between 20 and 10 000, for example between 30 and 1000. The length of the heating tube is understood to mean the length of the tube over which the microwave irradiation proceeds. Baffles and/or other mixing elements can be incorporated into the heating tube.

$E_{01}$ cavity resonators particularly suitable in accordance with the invention preferably have a diameter which corresponds to at least half the wavelength of the microwave radiation used. The diameter of the cavity resonator is preferably 1.0 to 10 times, more preferably 1.1 to 5 times and especially 2.1 to 2.6 times half the wavelength of the microwave radiation used. The $E_{01}$ cavity resonator preferably has a round cross section, which is also referred to as an $E_{01}$ round hollow conductor. It more preferably has a cylindrical shape and especially a circular cylindrical shape.

The residence time of the reaction mixture in the heating zone depends on various factors, for example the geometry of the heating tube, the incident microwave energy, the specific microwave absorption of the reaction mixture and the desired reaction temperature. The residence time of the reaction mixture in the heating zone is typically less than 30 minutes, preferably between 0.01 second and 15 minutes, more preferably between 0.1 second and 10 minutes and especially between 1 second and 5 minutes, for example between 5 seconds and 2 minutes. The intensity (power) of the microwave radiation is adjusted such that the reaction mixture when leaving the heating zone has the desired reaction temperature.

The microwave power to be injected into the cavity resonator for the performance of the process according to the invention depends especially on the target reaction temperature, but also on the geometry of the heating tube and hence the reaction volume and the flow rate of the reaction mixture through the heating zone. The microwave power to be injected is typically between 200 W and several hundreds of kW and especially between 500 W and 100 kW, for example between 1 kW and 70 kW. It can be generated by means of one or more microwave generators. To optimize the space-time yield, the microwave power is preferably adjusted such that the reaction mixture attains the desired reaction temperature within a very short time, but without resulting in electrical discharges in the microwave applicator.

Preferably, the temperature rise caused by the microwave irradiation is limited to a maximum of 500° C. at least for reactions in organic chemistry, for example by regulating the microwave intensity and/or the flow rate. For inorganic reactions, higher temperatures can also be established. It has been found to be particularly useful to perform the process according to the invention at temperatures between 70° C. and a maximum of 400° C., especially at temperatures between 120 and not more than 330° C. and especially between 150 and not more than 300° C., for example at temperatures between 180 and 270° C.

In the heating zone, reactant, product, any by-product and, if present, solvent can lead to a pressure buildup as a result of the temperature increase. This elevated pressure is preferably not released until after passage through the reaction zone, and the decompression can be used to volatilize and remove excess reactant(s), product, by-product and any solvent and/or to cool the reaction product.

The conversion of the reaction mixture often already begins in the heating zone, but is typically not yet at chemical equilibrium at the end thereof. On attainment of the reaction temperature, the reaction mixture is transferred directly, i.e. without intermediate cooling, from the heating tube to the isothermal reaction zone. The temperature difference between departure from the heating zone and entry into the isothermal reaction zone is thus preferably less than ±30° C., preferably less than ±20° C., more preferably less than ±10° C. and especially less than ±5° C. In a specific embodiment, the temperature of the reaction mixture on entry into the reaction zone corresponds to the temperature on departure from the heating zone. In a further specific embodiment, further reactants and/or assistants can be added to the reaction mixture before it enters the isothermal reaction zone.

The direct connection between the heating zone and the isothermal reaction zone is understood to mean a connection which does not have any active measures for supply and more particularly for removal of heat.

Useful isothermal reaction zones include all chemically inert vessels which enable residence of the reaction mixtures at the temperature established in the heating zone. An isothermal reaction zone is understood to mean that the temperature of the reaction mixture in the reaction zone relative to the entrance temperature is kept constant within ±30° C., preferably within ±20° C., more preferably within ±10° C. and especially within ±5° C. Thus, the reaction mixture when leaving the reaction zone has a temperature which deviates from the temperature on entry into the reaction zone by not more than ±30° C., preferably ±20° C., more preferably ±10° C. and especially ±5° C.

In addition to continuous stirred tanks and tank cascades, especially tubes are suitable as the isothermal reaction zone. These reaction zones may consist of different materials, for example metals, ceramic, glass, quartz or plastics, with the proviso that they are mechanically stable and chemically inert under the selected temperature and pressure conditions. It has been found that thermally insulated vessels are particularly useful. The residence time of the reaction mixture in the reaction zone can be adjusted, for example, via the volume of the reaction zone. In the case of use of stirred tanks and tank cascades, it has been found to be equally useful to establish the residence time via the fill level of the tanks.

In a preferred embodiment, the reaction zone used is a tube. This may be an extension of the microwave-transparent heating tube, or else a separate tube of the same or different material connected to the heating tube. For a given flow rate, the residence time of the reaction mixture can be determined over the length of the tube and/or cross section thereof. The tube which functions as the reaction zone is thermally insulated in the simplest case, such that the temperature which exists on entry of the reaction mixture into the reaction zone is held within the limits given above. However, it is also possible, for example by means of a heat carrier or cooling medium, to supply energy in a controlled manner to the reaction mixture in the reaction zone, or remove it therefrom. This embodiment has been found to be useful especially for startup of the apparatus or of the process, and for performance of strong endothermic or exothermic reactions. For example, the reaction zone may be configured as a tube coil or tube bundle which is within a heating or cooling bath or is charged with a heating or cooling medium in the form of a jacketed tube. The reaction zone may also be within a further microwave applicator in which the reaction mixture is treated once again with microwaves. In this case, it is possible to use either monomode or multimode applicators.

The residence time of the reaction mixture in the reaction zone depends on the reaction rate of the reaction conducted and the rate of any unwanted side reactions. In the ideal case, the residence time in the reaction zone is such that the thermal equilibrium state defined by the prevailing conditions is just attained. Typically, the residence time is between 1 second and 10 hours, preferably between 10 seconds and 2 hours, more preferably between 20 seconds and 60 minutes, for example between 30 seconds and 30 minutes.

In a preferred embodiment, the reaction mixture, immediately after leaving the isothermal reaction zone, is cooled very rapidly to temperatures below 120° C., preferably below 100° C. and especially below 60° C. This can be accomplished, for example, by means of heat exchangers, adiabatic expansion or dilution with cold solvent.

The inventive apparatus is typically provided at the inlet at least with a metering pump and a manometer. At the transition between heating zone and isothermal reaction zone is preferably at least one thermometer. To increase the safety of apparatus and process, it has been found to be useful to additionally install a non-return valve in the transition between heating zone and isothermal reaction zone. Relatively long isothermal reaction zones can also be divided into several segments by further non-return valves. In a preferred embodiment, the reaction zone is safeguarded against overpressure by at least one pressure-release device. At the outlet of the isothermal reaction zone, the reaction mixture is cooled and decompressed. For this purpose, the inventive apparatus is typically provided at least with a pressure-retaining device, a thermometer and a cooling device, for example a heat exchanger. Typically, the reaction mixture is decompressed to atmospheric pressure, but it can also be decompressed to higher or lower pressures for subsequent process steps or in the case of use of specific apparatuses. For example, it has been found to be useful to decompress the reaction mixture to pressures well below atmospheric pressure for removal of solvent and/or unconverted reactants. Depending on the properties of the converted products and the further process steps provided, the cooling can be effected before or else after lowering the pressure, or at an intermediate pressure.

The preparation of the reaction mixtures can be performed continuously, batchwise, or else in semi-batchwise processes. For instance, the preparation of the reaction mixture can be performed in an upstream (semi)batchwise process, for example in a stirred tank. The reaction mixture is preferably produced in situ and not isolated. In a preferred embodiment, the reactants, independently optionally diluted with solvent, are not mixed until shortly before entry into the reaction tube. For instance, it has been found to be particularly useful to combine the components of the reaction mixture in a mixing zone, from which they are conveyed into the heating zone, optionally after intermediate cooling. Additionally preferably, the reactants are supplied to the process according to the invention in liquid form. For this purpose, it is possible to use relatively high-melting and/or relatively high-viscosity reactants, for example in the molten state and/or admixed with solvent, for example as a solution, dispersion or emulsion. A catalyst, if used, can be added to one of the reactants or else to the reactant mixture before entry into the heating tube. It is also possible to convert heterogeneous systems by the process according to the invention, in which case appropriate technical devices are required to convey the reaction mixture.

To avoid side reactions and to prepare very pure products, it has been found to be useful to handle reactants and products in the presence of an inert protective gas, for example nitrogen, argon or helium.

The reaction mixture can be fed into the reaction tube either at the end passed through the inner conductor tube or at the opposite end. The reaction mixture can consequently be conducted parallel or antiparallel to the direction of propagation of the microwaves through the microwave applicator.

To perform the process according to the invention, through selection of the tube cross section, length of the heating zone (this is understood to mean the zone of the tube in which the reaction mixture is exposed to microwave radiation), flow rate, geometry of the cavity resonator and the incident microwave power, the reaction conditions are preferably adjusted such that the desired reaction temperature is attained as rapidly as possible. The reaction conditions desired for individual chemical reactions are preferably regulated by controlling the temperature of the reaction mixture attained at the end of the heating zone via the incident microwave power and/or via the flow rate of the reaction mixture through the heating zone. The pressure is adjusted via the decompression valve (pressure-retaining device) at the end of the reaction zone to a sufficiently high level that the reaction mixture including products and by-products obtained does not boil.

The process is performed preferably at pressures between 1 bar (atmospheric pressure) and 500 bar and more preferably between 1.5 and 200 bar, particularly between 3 bar and 150 bar and especially between 10 bar and 100 bar, for example between 15 bar and 50 bar. It has been found to be particularly useful to work under elevated pressure, in which case the temperature employed is above the boiling temperature (at standard pressure) of the reactants, products, of any solvent present and/or of the products formed during the reaction. The pressure is more preferably adjusted to a sufficiently high level that the reaction mixture remains in the liquid state and does not boil during the microwave irradiation.

The inventive apparatus and the inventive process allow a very rapid, energy-saving and inexpensive performance of chemical reactions in high yields in industrial scale amounts. The advantages of the inventive process lie especially in very rapid and nevertheless controlled heating of the reaction mixture by means of microwaves to the target reaction temperature without significant exceedance of the average temperature of the reaction mixture, for example at the vessel wall. This is particularly pronounced in the case of irradiation of the reaction mixture in the center of a symmetric microwave field within a reaction tube, the longitudinal axis of which is in the direction of propagation of the microwaves of a monomode microwave applicator, and especially within an $E_{01}$ cavity resonator, for example with a coaxial transition of the microwaves. With the inventive apparatus, in contrast to conventional heating techniques with heat transfer by means of a temperature gradient, it is possible to heat the reaction mixture virtually up to the decomposition temperature of the most thermally sensitive component and then to maintain this temperature until the equilibrium state which exists for these conditions is established.

In the isothermal reaction zone, the actual reaction or the completion of the reaction can take place without further external thermal stress on the reaction mixture. At the same time, the inventive apparatus allows the performance of reactions also at very high pressures and/or temperatures.

In the inventive apparatus and in the process which uses it, a very high efficiency is achieved in the exploitation of the microwave energy injected into the cavity resonator, and is typically above 50%, often above 80%, in some cases above 90% and in special cases above 95%, for example above 98%, of the incident microwave power, and thus offers economic and environmental advantages over conventional preparation processes, and also over prior art microwave processes.

Inventive apparatus and process additionally allow, through the continuous microwave irradiation of only small amounts of reaction mixture, a controlled, safe and reproducible reaction regime. Especially in the case of irradiation of the reaction mixture in the center of a symmetric microwave field within a reaction tube whose longitudinal axis is in the direction of propagation of the microwaves of a monomode microwave applicator, the reaction mixture during the microwave irradiation is moved parallel to the direction of propagation of the microwaves. Thus, known overheating phenomena resulting from uncontrollable field distributions which lead to local overheating as a result of varying intensities of the microwave field, for example at wave crests and node points, are balanced out by the flowing motion of the reaction mixture. The advantages mentioned also allow working with high microwave powers of, for example, more than 10 kW or more than 100 kW, and thus, in combination with only a short residence time in the heating tube, the accomplishment of large production volumes of 100 or more tonnes per year in one plant. The isothermal reaction zone achieves optimization of the space-time yield by subsequent establishment of the chemical equilibrium, since no increase in the residence time in the irradiation zone by lowering the flow rate is required. Thus, on the other hand, an increased throughput in the heating zone is possible compared to the same apparatus without a reaction zone, which further improves the economic viability of such a microwave-supported process.

At the same time, it was surprising that, in spite of the only very short residence time of the reaction mixture in the microwave field in the flow tube with continuous flow, a distinct increase in the conversion of the reactants was achievable through the use of an additional reaction zone, without formation of significant amounts of by-products. In the case of an appropriate conversion of the reaction mixture in a flow tube of the same dimensions with thermal jacket heating, achievement of suitable reaction temperatures requires extremely high wall temperatures which often led to the formation of colored species. It was additionally surprising that the conversions mentioned can be achieved in condensation reactions such as amidations and esterifications under these reaction conditions without removal of the water of reaction formed in the condensation. In addition, the products prepared by the process according to the invention typically have very low metal contents without any requirement for further workup of the crude products. For instance, the metal contents of the products prepared by the process according to the invention, based on iron as the main element, are typically below 25 ppm, preferably below 15 ppm, especially below 10 ppm, for example between 0.01 and 5 ppm of iron.

Figure 1:
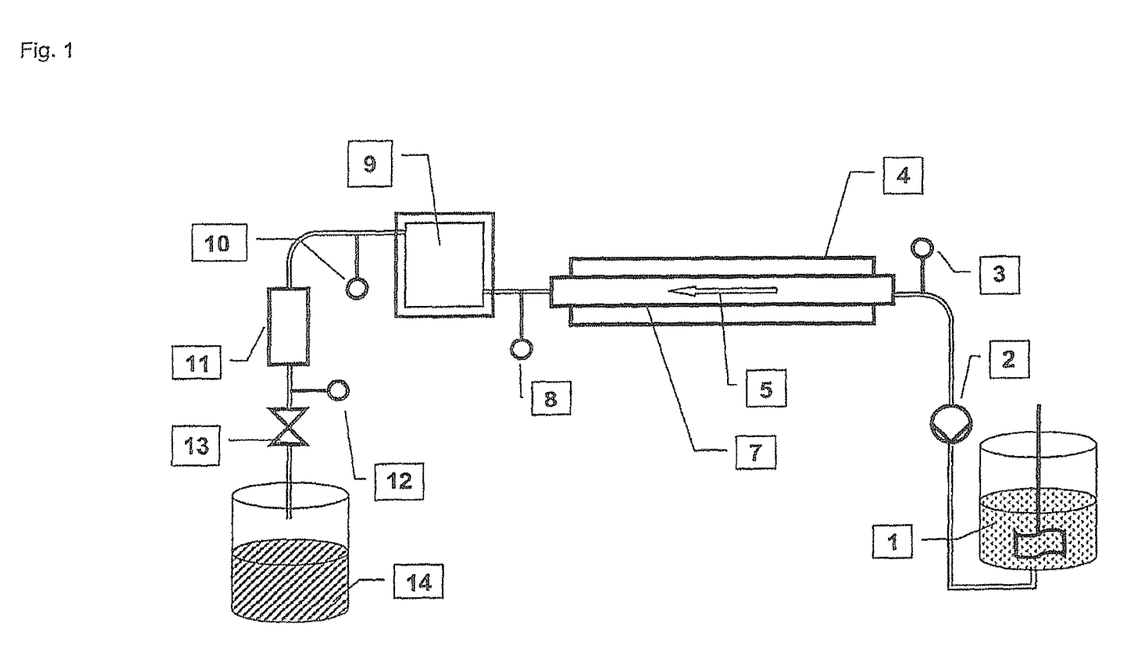
FIG. 1 is a schematic representation of an apparatus for continuously performing chemical reactions, comprising a microwave generator.

FIG. 1 shows one example of an inventive apparatus. It comprises a stirred reactant reservoir (1), which provides the reaction mixture via a conveying line with conveying pump (2). Before the entry of the reaction mixture into the heating tube (7) manufactured from microwave-transparent material, the temperature and pressure of the reaction mixture are determined at a measurement point (3). The reaction mixture flows through the heating tube (7) in the specified direction (5). The heating tube is within a microwave applicator (4). At the end of the heating zone is a measurement point for temperature and optionally pressure (8). Immediately after leaving the heating tube (4), the reaction mixture is transferred into the isothermal reaction zone (9). At the outlet of the isothermal reaction zone (9) is a measurement point for temperature (10). Beyond the isothermal reaction zone is mounted a cooler (11), followed by a measurement point for pressure and temperature (12). After passing through the cooler, the product passes through a decompression valve (13) into the product receiver (14).

Figure 2:
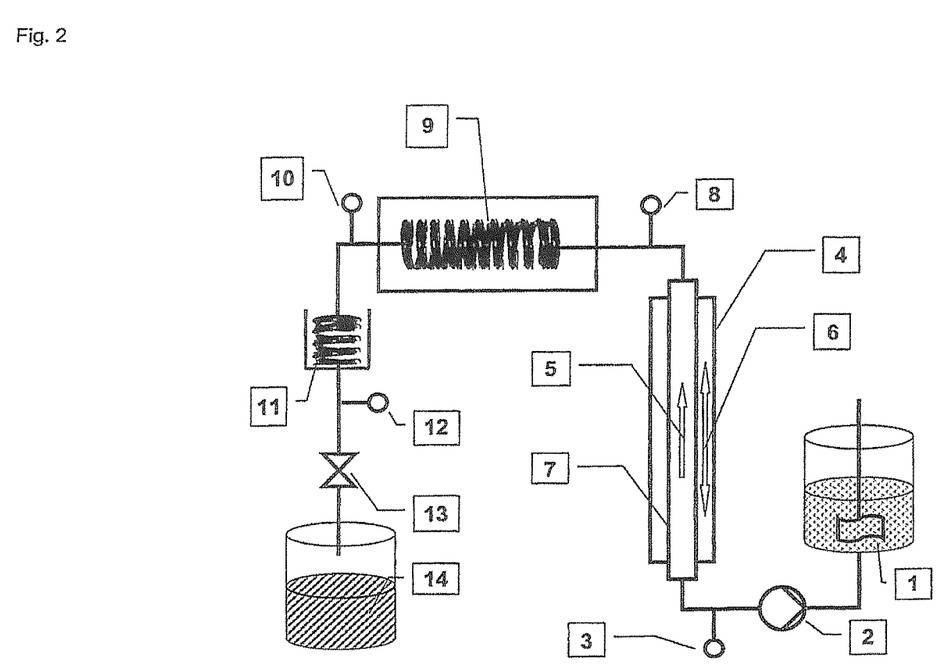
FIG. 2 is a schematic drawing of an alternative arrangement of an apparatus for continuously performing chemical reactions, comprising a microwave generator.

FIG. 2 shows one example of a further inventive apparatus, in which the microwave oven (4) used is a monomode applicator in which the direction of propagation of the microwaves (6) is parallel or antiparallel to the flow direction of the reaction mixture (5). The isothermal reaction zone (9) and the cooler (11) are configured here as tube coils.

EXAMPLES

The irradiations of the reaction mixtures with microwaves were effected in an apparatus which contained, as a heating tube, a ceramic tube (60×1 cm) which was present in axial symmetry in a cylindrical cavity resonator (60×10 cm). At one of the ends of the cavity resonator, this heating tube ran through the cavity of an inner conductor tube which functions as a coupling antenna. The microwave field with a frequency of 2.45 GHz, generated by a magnetron, was injected into the cavity resonator by means of the coupling antenna ($E_{01}$ cavity applicator; monomode), in which a standing wave formed. The heated reaction mixtures immediately thereafter were conveyed through a thermally insulated stainless steel tube (3.0 m×1 cm, unless stated otherwise). After leaving this reaction tube, the reaction mixtures were decompressed to atmospheric pressure and cooled immediately to approx. 60° C. by means of an intensive heat exchanger.

The microwave power was adjusted over the experimental duration in each case in such a way that the desired temperature of the reaction mixture at the end of the heating zone was kept constant. The microwave powers specified in the experimental descriptions therefore represent the mean value of the incident microwave power over time. The measurement of the temperature of the reaction mixture was undertaken by means of a Pt100 temperature sensor immediately after departure from the heating zone (distance about 15 cm in an insulated stainless steel capillary, Φ 1 cm) and after departure from the reaction zone. Microwave energy not absorbed directly by the reaction mixture was reflected at the opposite end of the cavity resonator from the coupling antenna; the microwave energy which was also not absorbed by the reaction mixture on the return path and reflected back in the direction of the magnetron was passed with the aid of a prism system (circulator) into a water-containing vessel. The difference between energy injected and heating of this water load was used to calculate the microwave energy introduced into the reaction mixture.

By means of a high-pressure pump and of a suitable pressure-release valve, the reaction mixture in the apparatus was placed under such a working pressure that was sufficient always to keep all reactants and products or condensation products in the liquid state. The reaction mixtures were pumped through the apparatus at a constant flow rate and the residence time in the heating zone and reaction zone was adjusted by modifying the flow rate.

The products were analyzed by means of $^1$H NMR spectroscopy at 500 MHz in $CDCl_3$.

Example 1

Preparation of N-(3-(N,N-dimethylamino)propyl)laurylamide

A 10 l Büchi stirred autoclave with stirrer, internal thermometer and pressure equalizer was initially charged with 3.4 kg of lauric acid (17 mol), which were heated to 60° C. and admixed cautiously, while cooling gently, with 2.6 kg of N,N-dimethylaminopropylamine (25.5 mol).

The mixture thus obtained was pumped continuously through the apparatus at 10.0 l/h at a working pressure of 35 bar, and exposed in the heating zone to a microwave power of 4.8 kW, 94% of which was absorbed by the reaction mixture. The residence time of the reaction mixture in the heating zone was approx. 17 seconds, the residence time in the reaction zone approx. 85 seconds. At the end of the heating zone the reaction mixture had a temperature of 296° C., and after leaving the reaction zone a temperature of 292° C.

A conversion of fatty acid of 97% of theory was attained. The reaction product was pale yellowish in color; the iron content of the product was below 5 ppm. After distillative removal of water of reaction and excess N,N-dimethylaminopropylamine, 4.6 kg of N-(3-(N,N-dimethylamino)propyl)laurylamide with a purity sufficient for direct further use (quaternization) were obtained.

Example 2

Preparation of N,N-diethylcocoamide

A 10 l Büchi stirred autoclave with gas inlet tube, stirrer, internal thermometer and pressure equalizer was initially charged with 4.2 kg of coconut fat (5.5 mol/molecular weight 764 g/mol), which were heated to 45° C. At this temperature, 2.0 kg of diethylamine (27 mol) and 100 g of sodium ethoxide as a catalyst were added gradually, and the mixture was homogenized while stirring.

The reaction mixture thus obtained was pumped continuously through the apparatus at 5.5 l/h at a working pressure of 32 bar, and exposed in the heating zone to a microwave power of 2.7 kW, 90% of which was absorbed by the reaction mixture. The residence time of the reaction mixture in the heating zone was approx. 31 seconds, the residence time in the reaction zone approx. 155 seconds. At the end of the heating zone the reaction mixture had a temperature of 260° C., and after leaving the reaction zone a temperature of 258° C.

The reaction product was pale yellowish in color. After distillative removal of excess diethylamine, neutralization of the catalyst with dilute acetic acid and removal of the glycerol/water phase formed, 4.66 kg of N,N-diethylcocoamide with a purity of >97% were obtained.

Example 3

Preparation of Rapeseed Oil Methyl Ester

A 10 l Büchi stirred autoclave with stirrer, internal thermometer and pressure equalizer was initially charged with 3.1 kg of rapeseed oil fatty acid (10 mol, MW 309 g/mol), and 2.58 kg of methanol (80 mol) and 0.075 kg of methanesulfonic acid were added.

The mixture thus obtained was pumped continuously through the apparatus at 10.0 l/h at a working pressure of 35 bar, and exposed in the heating zone to a microwave power of 2.6 kW, 92% of which was absorbed by the reaction mixture. The residence time of the reaction mixture in the heating zone was approx. 17 seconds, the residence time in the reaction zone approx. 86 seconds. At the end of the heating zone the reaction mixture had a temperature of 251° C., and after leaving the reaction zone a temperature of 245° C.

A conversion of the fatty acid of 97% of theory was attained. The reaction product was pale yellowish in color; its iron content was below 5 ppm. After neutralization of the catalyst with hydrogencarbonate solution, distillative removal of the excess methanol and subsequent washing out of water-soluble salts, 3.1 kg of rapeseed oil methyl ester with a residual acid number of 0.2 mg KOH/g were obtained.

Example 4

Suzuki Coupling

A 1 liter three-neck flask with nitrogen inertization was initially charged with 500 ml of ethanol, and 50 g of tetrakis (triphenylphosphine)palladium(0) (44 mmol) were finely suspended therein with vigorous stirring. A nitrogen-inertized 10 l Büchi stirred autoclave with stirrer, internal thermometer and pressure equalizer was initially charged with 2 liters of an ethanol/water/dimethylformamide mixture, and 376 g of 4-bromotoluene (2.2 mol) and 244 g (2.0 mol) of phenylboronic acid were dissolved therein. Subsequently, the catalyst suspension was added gradually to the stirred autoclave with nitrogen inertization and stirred in homogeneously. The easily pumpable suspension thus obtained was pumped continuously through the apparatus at 1.5 l/h at a working pressure of 30 bar, and exposed in the heating zone to a microwave power of 1.2 kW, 92% of which was absorbed by the reaction mixture. The residence time of the reaction mixture in the heating zone was approx. 113 seconds, and the residence time in the reaction zone approx. 10 minutes. At the end of the heating zone the reaction mixture had a temperature of 255° C., and after leaving the reaction zone a temperature of 251° C.

A yield determined by means of $^1$H NMR (based on the phenylboronic acid used in deficiency) of 72% of theory was attained; the iron content of the product was <5 ppm. The catalyst and insoluble by-products were removed from the crude product by filtration, and then the filtrate was worked up by distillation. On completion of workup, 256 g of 4-methylbiphenyl with a purity of >98% were obtained.

Example 5

Preparation of poly(isobutenyl)succinic Anhydride

A 10 l Büchi stirred autoclave with stirrer, internal thermometer and pressure equalizer was initially charged with 4.0 kg of poly(isobutylene) (Glissopal® 1000, BASF AG, with molar mass 1000, content of alpha-double bonds: 80%; 4.0 mol), 431 g of maleic anhydride (4.4 mol) were added and the mixture was heated to about 70° C. while stirring.

The low-viscosity emulsion thus obtained was pumped continuously through the apparatus at 2.0 l/h at a working pressure of 30 bar, and exposed in the heating zone to a microwave power of 1.8 kW, 90% of which was absorbed by the reaction mixture. The residence time of the reaction mixture in the heating zone was approx. 85 seconds. The reaction zone employed here was a tube with a diameter of 2 cm and a length of 10 meters, such that a residence time in the reaction zone of approx. 94 minutes was attained. At the end of the heating zone the reaction mixture had a temperature of 240° C., and after leaving the reaction zone a temperature of 235° C.

A conversion of 82% of the poly(isobutylene) used was attained. The iron content of the product was <5 ppm. Visual examination of the internal walls of heating zone and reaction zone after completion of the experiment did not reveal any deposits indicating coking or decomposition in either apparatus part, as regularly occur in reactions conducted thermally in a conventional manner.

Examples 1C to 5C

Comparative Experiments without Use of a Reaction Zone

In these experiments, experiments 1 to 5 were repeated, except with the above-described heating zone, i.e. without use of a reaction tube. The corresponding experimental parameters are compiled in table 1. The temperatures specified are based on the values measured on departure from the heating zone.

| Experiment | Throughput [l/h] | μw power [kW] | Residence time in heating zone [sec] | Temperature downstream of heating zone [° C.] | Conversion or yield |
|---|---|---|---|---|---|
| 1 | 10.0 | 4.8 | 17 | 296 | 97% |
| 1C | 5.6 | 3.1 | 30 | 280 | 93% |
| 2 | 5.5 | 2.7 | 31 | 260 | 4.66 kg |
| 2C | 4.5 | 2.2 | 38 | 265 | 3.70 kg |
| 3 | 10.0 | 2.6 | 17 | 251 | 97% |
| 3C | 7.5 | 3.0 | 23 | 279 | 91% |
| 4 | 1.5 | 1.2 | 113 | 255 | 72% |
| 4C | 1.0 | 1.0 | 170 | 267 | 42% |
| 5 | 2.0 | 1.8 | 85 | 240 | 82% |
| 5C | 1.0 | 1.2 | 170 | 245 | 26% |

The invention claimed is:

1. An apparatus for continuously performing a chemical reaction, comprising a microwave generator, a monomode microwave applicator with a microwave-transparent tube within, and an isothermal reaction zone, which are arranged such that the longitudinal axis of the microwave-transparent tube is in the direction of propagation of the microwaves in the monomode microwave applicator, and that a reaction mixture in the microwave-transparent tube is conducted through the monomode microwave applicator as a heating zone, within which the reaction mixture is heated to reaction temperature by means of microwaves which are conducted out of the microwave generator into the monomode microwave applicator, and wherein the heated and the optionally pressurized, reaction mixture is transferred immediately after leaving the heating zone into the isothermal reaction zone adjoining the heating zone and, after leaving the isothermal reaction zone, the reaction mixture is cooled down.

2. The apparatus as claimed in claim 1, in which the microwave-transparent tube is within a hollow conductor as a microwave applicator connected to a microwave generator.

3. The apparatus as claimed in claim 1, in which the microwave applicator is configured as a cavity resonator.

4. The apparatus as claimed in claim 1, in which the microwave applicator is configured as a reflection-type cavity resonator.

5. The apparatus as claimed in claim 2, in which the microwave-transparent tube is aligned axially with a central axis of symmetry of the hollow conductor.

6. The apparatus as claimed in claim 3, in which the cavity resonator has a coaxial transition of the microwaves.

7. The apparatus as claimed in claim 3, in which the cavity resonator is operated in $E_{01n}$ mode where n is an integer from 1 to 200.

8. The apparatus as claimed in claim 1, wherein the isothermal reaction zone is a thermally insulated tube.

9. The apparatus as claimed in claim 1, in which the isothermal reaction zone comprises an apparatus for supply or removal of energy.

10. A process for continuously performing a chemical reaction, in which the reaction mixture, in an apparatus as claimed in claim 1, is conducted through a heating zone in which it is heated to reaction temperature by microwaves and from which the heated and optionally pressurized reaction mixture is transferred immediately after leaving the heating zone into an isothermal reaction zone adjoining the heating zone and, after leaving the isothermal reaction zone, is cooled.

11. The process as claimed in claim 10, in which the reaction mixture is heated by the microwaves to temperatures between 70 and 500° C.

12. The process as claimed in claim 10, in which the microwaves are effected at pressures above atmospheric pressure.

13. The process as claimed in claim 10, in which the properties of the isothermal reaction zone are such that the temperature of the reaction mixture after passing through the isothermal reaction zone differs by at most ±20° C. from the inlet temperature of the heating zone.

14. The process for continuously performing a chemical reaction in an apparatus as claimed in claim 3 in which a standing wave forms in the cavity resonator.

* * * * *